United States Patent [19]
McCormack et al.

[11] Patent Number: 5,882,769
[45] Date of Patent: Mar. 16, 1999

[54] STRETCH-PILLOWED, BULKED LAMINATE

[75] Inventors: Ann Louise McCormack, Cumming, Ga.; Duane Girard Uitenbroek, Little Chute, Wis.

[73] Assignee: Kimberly-Clark Worldwide, Inc., Neenah, Wis.

[21] Appl. No.: 814,495

[22] Filed: Mar. 10, 1997

Related U.S. Application Data

[60] Continuation of Ser. No. 449,617, May 23, 1995, abandoned, which is a division of Ser. No. 357,365, Dec. 15, 1994, abandoned, which is a continuation of Ser. No. 997,800, Dec. 29, 1992, abandoned.

[51] Int. Cl.$^6$ .................................................. B32B 27/14
[52] U.S. Cl. ......................... 428/152; 156/160; 156/163; 156/164; 156/229; 156/290; 156/291; 156/308.2; 156/308.4; 156/308.6; 156/73.1; 428/138; 428/198; 442/394; 604/358; 604/365
[58] Field of Search .................................. 428/152, 198, 428/138; 442/62, 394; 604/358, 365; 156/160, 163, 290, 291, 308.2, 308.4, 308.6, 73.1

[56] References Cited

U.S. PATENT DOCUMENTS

| | | | |
|---|---|---|---|
| 3,276,944 | 10/1966 | Levy | 161/150 |
| 3,316,136 | 4/1967 | Pufahl | 156/160 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |

(List continued on next page.)

FOREIGN PATENT DOCUMENTS

| | | | |
|---|---|---|---|
| 803714 | 1/1969 | Canada . | |
| 2025186 | 3/1991 | Canada . | |
| 0 066 672 | 12/1982 | European Pat. Off. | C08J 5/18 |
| 0 192 965 A1 | 9/1986 | European Pat. Off. . | |
| 0 302 597 A2 | 2/1989 | European Pat. Off. . | |
| 0 307 116 B1 | 3/1989 | European Pat. Off. . | |
| 0 323 629 A2 | 7/1989 | European Pat. Off. | C08J 5/18 |
| 0 309 073 | 8/1989 | European Pat. Off. | B23B 27/12 |
| 0403187A1 | 12/1990 | European Pat. Off. . | |
| 0 409 567 A2 | 1/1991 | European Pat. Off. | B29C 49/08 |
| 0444671A2 | 2/1991 | European Pat. Off. . | |
| 0257280B1 | 9/1991 | European Pat. Off. . | |
| 0505027A1 | 9/1992 | European Pat. Off. . | |
| 0 084 903 A3 | 8/1993 | European Pat. Off. . | |
| 0556749 | 8/1993 | European Pat. Off. . | |
| 2260716 | 5/1974 | Germany . | |
| 3306846 | 2/1983 | Germany . | |
| 3724510A1 | 2/1989 | Germany . | |
| 61-072543 | 4/1986 | Japan | B32B 5/18 |
| 1144431 | 6/1989 | Japan | B29C 55/12 |
| 2036938 | 2/1990 | Japan | A41B 13/02 |
| 2282003 | 11/1990 | Japan | B65B 9/06 |
| 4-227260 | 8/1992 | Japan . | |
| 793072 | 6/1979 | South Africa . | |
| 2 115 702 | 9/1983 | United Kingdom | A61F 13/16 |
| 2 155 853 | 10/1985 | United Kingdom | B32B 5/18 |
| 2 285 408 | 7/1995 | United Kingdom | C08J 5/18 |
| 2 290 052 | 12/1995 | United Kingdom | B32B 27/12 |
| WO9006228 | 6/1990 | WIPO . | |
| 93/11726 | 6/1993 | WIPO . | |
| 93/11725 | 6/1993 | WIPO . | |
| 93/21013 | 10/1993 | WIPO | B32B 27/12 |

*Primary Examiner*—James J. Bell
*Attorney, Agent, or Firm*—Patrick C. Wilson

[57] ABSTRACT

Disclosed herein is a bulk-stretched pillowed laminate of two or more layers in which at least one of the layers is stretched before other layers are attached to it. In one execution, a thermoplastic film is stretched until it permanently deforms. Then, while still in a stretched state, a nonwoven web is laminated to the film and the resultant composite is allowed to relax slightly causing the nonwoven layer to gather and pucker, which in turn gives the composite a thicker and bulkier feel and appearance. The material of the present invention, while having a wide variety of uses, is particularly well-suited for use as an outercover for personal care absorbent articles, including diapers, training pants and sanitary napkins.

36 Claims, 2 Drawing Sheets

U.S. PATENT DOCUMENTS

| | | | |
|---|---|---|---|
| 3,542,615 | 11/1970 | Dobo et al. | 156/181 |
| 3,676,242 | 7/1972 | Prentice | 156/62.4 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,949,128 | 4/1976 | Ostermeier | 428/152 |
| 3,973,063 | 8/1976 | Clayton | 428/35 |
| 4,041,203 | 8/1977 | Brock et al. | 428/157 |
| 4,042,740 | 8/1977 | Krueger | 428/138 |
| 4,081,301 | 3/1978 | Buell | 156/164 |
| 4,087,486 | 5/1978 | Fielding et al. | 250/897 |
| 4,104,404 | 8/1978 | Bieler et al. | 428/35 |
| 4,144,370 | 3/1979 | Boulton | 428/233 |
| 4,185,135 | 1/1980 | Huff | 428/96 |
| 4,254,175 | 3/1981 | Kubat et al. | 428/213 |
| 4,297,157 | 10/1981 | Van Vliet | 156/164 |
| 4,300,967 | 11/1981 | Sigl | 156/164 |
| 4,340,563 | 7/1982 | Appel et al. | 264/518 |
| 4,348,444 | 9/1982 | Craig | 428/137 |
| 4,379,192 | 4/1983 | Wahlquist et al. | 428/156 |
| 4,443,513 | 4/1984 | Meitner et al. | 422/195 |
| 4,446,189 | 5/1984 | Romanek | 428/152 |
| 4,522,203 | 6/1985 | Mays | 128/132 |
| 4,525,407 | 6/1985 | Ness | 428/138 |
| 4,595,629 | 6/1986 | Mays | 428/286 |
| 4,606,964 | 8/1986 | Wideman | 428/152 |
| 4,606,970 | 8/1986 | Sharps, Jr. | 428/301 |
| 4,626,252 | 12/1986 | Nishizawa | 604/370 |
| 4,650,481 | 3/1987 | O'Connor et al. | 604/380 |
| 4,657,802 | 4/1987 | Morman | 428/152 |
| 4,681,793 | 7/1987 | Linman et al. | 428/138 |
| 4,692,368 | 9/1987 | Taylor et al. | 428/137 |
| 4,720,415 | 1/1988 | Vander Wielen et al. | 428/152 |
| 4,725,473 | 2/1988 | Van Gompel et al. | 428/156 |
| 4,741,944 | 5/1988 | Jackson et al. | 428/152 |
| 4,761,324 | 8/1988 | Rautenberg et al. | 428/198 |
| 4,822,350 | 4/1989 | Ito et al. | 604/372 |
| 4,883,549 | 11/1989 | Frost et al. | 156/161 |
| 4,929,303 | 5/1990 | Sheth | 156/209 |
| 4,935,287 | 6/1990 | Johnson et al. | 428/198 |
| 4,981,747 | 1/1991 | Morman | 428/198 |
| 4,983,450 | 1/1991 | Yanagihara et al. | 428/283 |
| 5,011,698 | 4/1991 | Antoon, Jr. et al. | 426/395 |
| 5,114,781 | 5/1992 | Morman | 428/198 |
| 5,116,662 | 5/1992 | Morman | 428/198 |
| 5,143,679 | 9/1992 | Weber et al. | 264/288 |
| 5,169,712 | 12/1992 | Tapp | 428/315 |
| 5,208,098 | 5/1993 | Stover | 428/284 |
| 5,244,716 | 9/1993 | Thorton et al. | 428/198 |
| 5,261,899 | 11/1993 | Visscher et al. | 604/367 |
| 5,336,552 | 8/1994 | Strack et al. | 428/224 |
| 5,352,216 | 10/1994 | Shiono et al. | 604/312 |

STRETCH-PILLOWED, BULKED LAMINATE

This application is a continuation of application Ser. No. 08/449,617 entitled "STRETCH-PILLOWED, BULKED LAMINATE" and filed in the U.S. Patent and Trademark Office on May 23, 1995, which is a divisional application Ser. No. 08/357,365 entitled the same and filed in the U.S. Patent and Trademark Office on Dec. 15, 1994, which is a file wrapper continuation of application Ser. No. 07/997,800 entitled the same and filed Dec. 29, 1992, all now abandoned. The entirety of these applications are hereby incorporated by reference.

TECHNICAL FIELD OF THE INVENTION

The present invention relates to highly-bulked stretch-pillowed materials. More particularly, the present invention relates to laminates wherein at least one layer of the laminate has been stretched and in some cases permanently deformed and wherein at least a second layer has been attached to the first layer while the first layer is in a stretched condition.

BACKGROUND OF THE INVENTION

The materials of the present invention are suitable for a wide variety of applications where substantially three-dimensional, bulky, cloth-like materials are useful. This is in comparison to substantially two-dimensional materials and composites such as individual layers of film and/or nonwovens or plain laminates of such materials. While not meaning to limit the scope of the present invention, one area of particular usefulness for the materials of the present invention is in personal care absorbent articles such as diapers, incontinence garments, training pants, feminine pads, sanitary napkins, bandages and the like. Many of these materials are multi-layered structures which use tissue and wood based fibers as well as nonwovens and polymeric films to form specific layers of the overall structure. Oftentimes these layers can benefit from a more bulky feel. As an example, diapers employ a lining material which usually includes a polymeric nonwoven web made from a plurality of fibers bonded to one another. Such a liner material must be soft to the baby's touch for comfort while also being able to quickly absorb and then transfer body fluids to the absorbent interior core material. Generally, from a consumer's standpoint, the softer and bulkier the liner material is, the higher the perception will be of the quality and comfort of the material. In the same fashion, the backing of the diaper generally includes a plastic film or some other material to provide liquid-barrier properties so as to retain exuded body fluids. Sometimes this layer may include a nonwoven layer to impart a certain cloth-like feel thereby increasing both the quality and comfort of the overall product.

Consumer testing has indicated that three-dimensional, "bulky" materials are perceived as being of higher quality than "non-bulked" two-dimensional structures. Two dimensional structures are often the result of the lamination of two juxtaposed layers of film, nonwoven, tissue and/or other natural or synthetic based materials. Such two dimensional layers do not have a high degree of bulk as their combined thickness is usually equal to or less than the combined thicknesses of the individual layers prior to lamination. Quilted materials are frequently perceived by the consumers as having a higher degree of bulk, softness and comfort. Imparting a quilt-like look to the laminated layers usually involves either actually stitching the layers together or bonding the layers together with some type of three dimensional bond pattern. Here again, however, the overall thickness of the quilted product is generally no greater than the combined thicknesses of the joined layers as the quilting process usually results from the reduction in thickness of the combined layers in the areas where the quilting pattern has been imparted.

Another way to impart a more bulky feel and look to materials is to make an elastic laminate such as is taught in U.S. Pat. No. 4,720,415 issued to Taylor et al. and commonly assigned to the assignee of record, Kimberly-Clark Corporation. Materials such as these include an elastomeric material which forms a stretchable, elastic layer. To at least one side of this material while in a stretched condition there is attached another gatherable layer. Once the two layers have been attached to one another, the elastic layer is allowed to retract thereby gathering up and puckering the non-elastic gatherable layer to form more of a three-dimensional material. While such elastomeric materials are suitable for use in the same products as the present invention, they are definitely more costly due to the use of elastomeric polymers. The present invention overcomes this cost factor by using more less expensive materials. Furthermore in contrast to the materials taught in Taylor et al., the materials of the present invention once formed are non-elastic in nature.

It is therefore an object of the present invention to provide a material which while made from relatively flat planar two-dimensional materials creates more of a three-dimensional, bulky pillowed material once two or more layers have been attached to one another.

It is another object of the present invention to provide a material which can be made more three-dimensional in appearance while using relatively inexpensive components.

It is a further object of the present invention to provide a material with such properties which is substantially non-elastic.

It is yet another object of the present invention to provide a process for making such materials.

These and other objects of the present invention will become more apparent upon a further review of the following specification, drawings and claims.

SUMMARY OF THE INVENTION

This invention relates to a process for forming a bulked, stretch-pillowed laminate and the resultant laminate. The process involves extending a first extensible layer from an original length to an expanded length with the expanded length being at least 5 percent greater than the original length. Depending upon the degree of stretching, the first extensible layer may be permanently deformed. Next, a second layer of material is placed in juxtaposition with the first layer while the first layer is still in the expanded length and the two layers are then attached to one another at a plurality of spaced-apart bond sites to form the laminate which includes a plurality of bonded and unbonded areas. Once the laminate has been formed, the first layer is allowed to relax to a third length which is usually longer than the first length of the first layer. As a result of the attachment of the second layer to the first layer while the first layer is in an expanded state, once the laminate contracts, the first layer gathers and puckers, thereby forming a much bulkier material as compared to a simple non-stretched laminate of the same two materials.

While a number of material are suitable for use with the present invention, two specific combinations which work particularly well are where the first layer is a thermoplastic film and the second layer is a nonwoven fibrous web or, alternatively, where both the first and second layers are made from fibrous nonwoven webs. The film/nonwoven composite has the combined advantages of being liquid impervious while also providing a soft, bulky feel on one side of the material which makes the composite particularly useful as an outercover material for personal care products including diapers, training pants and incontinence garments. The nonwoven/nonwoven configuration also has particular usefulness in the area of personal care products as a liner material for such products.

In more refined embodiments of the present invention, the process may be further modified by adding yet an additional layer to the bulked, stretched-pillowed laminate material. For example, a third layer of material may be added to the side of the first layer (while the first layer is in a stretched condition) which is opposite the side to which there is attached the second layer. The attachment of the third layer to the first layer may be accomplished in at least two ways. The first way involves passing all three material through the same bonding equipment so that the bond points of the second and third layers to the first layer are in vertical registry with one another. The second way involves using two sets of bonding equipment such that the first and second layers are attached to one another in a first bonding process and then the third layer is added to the composite via a second bonding process such that the bond points between the first layer and the second layer are not in vertical registry with the bond points between the first and third layers. It also should be noted that depending upon the speeds at which the second and third layer are fed into the process, either or both of the second and third layers may be stretched, though generally it is desirable that their degree of stretch be less than that of the first layer. Furthermore, it is possible to stretch any one of the foregoing layers in more than one direction or in directions that are not parallel to one another with respect to the individual layers.

Attachment of the various layers to one another can be accomplished by a variety of means including adhesives, ultrasonic bonding, thermo-mechanical bonding, stitching, etc. Suitable adhesives include water-based, solvent-based, pressure-sensitive, and hot-melt adhesives.

Extension of the first layer can be from as little as 5% to as much as 1200% of the original length of the first layer. Usually, when stretching the first layer several hundred percent or more, the first layer will permanently deform such that upon relaxation of the stretching forces, the first layer only retracts a small portion of the distance that the first layer was initially stretched. As a result, the retracted or third length will oftentimes be between about 80 and 98% of the expanded length. A notable attribute of the material of the present invention, however, is that upon retraction of the first layer, the second layer will have a greater surface area than the first layer per the same unit area of the composite.

DETAILED DESCRIPTION OF THE INVENTION

The present invention is related to a highly-bulked, stretch-pillowed material formed by bonding, laminating or otherwise attaching two or more layers to one another. One of the layers is stretched and in some cases permanently deformed from a first or original length L1 to a second length L2 which is greater than its original length. After the first layer has been stretched, and while it is still in a tensioned condition, a second layer is attached to the first layer. Due to the nature of the stretching of the first layer, the first layer still has some degree of recovery. As a result, after the two layers have been attached to one another, the tension is released and the layers are allowed to retract slightly to a third length L3 which is greater than the first or original length L1 of the first layer yet slightly less than the second, stretched length L2 of the first layer. Due to the slight recovery of the first layer, the second layer tends to gather and form pillows thereby imparting a bulky, more three-dimensional appearance to the composite. This is because the second layer 14 has a larger surface area than the first layer 12 per the same unit area of the composite 10. In addition, there can be a savings in the amount of material used for the first layer as the first layer can be thinned during the stretching and deformation process. It should be understood that in the context of the present invention, the term "layer" can be meant to include a single piece or sheet of material as well as a laminate made from a plurality of individual sheets of material.

The material of the present invention has a wide variety of uses including, but not limited to, personal care applications such as diapers, feminine pads, training pants, adult incontinence products, sanitary napkins, bandages and the like. The material of the present invention also has applicability in the area of clothing due to the comfortable, bulky nature of the material. In addition, the material of the present invention has possible applications as a padded package and/or envelope material as well as a filter media. As a result, these and other applications are meant to be within the scope of the present invention and, therefore, the examples contained herein should be considered as illustrative only and not as limiting to the scope of the present invention.

Figure 1:
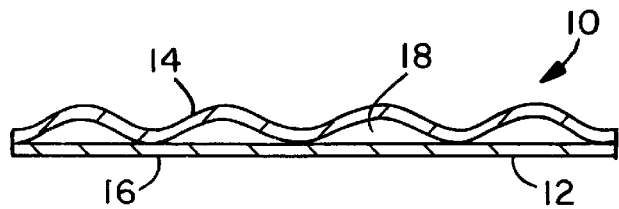
FIG. 1 is a cross-sectional side view of a stretch-pillowed laminate according to the present invention.

Turning to FIG. 1, the stretch-pillowed material 10 of the present invention includes a first extensible layer 12 and a second layer 14. By extensible it is meant that the material is capable of being stretched from a first or original length L1 to a second and greater length L2 and then, upon release of the stretching forces, the material retracts to a third length L3 which is less than the second length L2. The first and second layers 12 and 14 respectively can be made from a wide variety of materials including films, nonwoven materials, woven materials, knits, scrim and tissue. The films can be made from breathable or non-breathable materials. In addition the films can be apertured. In forming the films, the films may be coextruded to increase bonding and the films may be filled with an opacifying agent such as titanium dioxide. The nonwoven materials can be made from longer more continuous fibers such as spunbond and meltblown fibers or from shorter staple fibers such as are used in bonded carded webs. Suitable fibers include natural and synthetic fibers as well as bicomponent and multicomponent/polymer fibers. The nonwoven webs may be hydroentangled and they can be formed using any number of techniques including spunbonding, meltblowing, solution spinning and wet laying. In addition, laminated layers such as spunbond/meltblown/spunbond composites can be used for either the first or second layer. The woven and knit materials can be made from both synthetic and natural fibers. They also can be made from combinations of both natural and synthetic fibers. Tissue based layers are typically made from natural fibers such as pulp, but they can also include synthetic fibers.

Combinations of anyone of the foregoing materials may be employed for forming the material of the present invention. Examples of but a few combinations include: film/nonwoven; film/woven; film/knit; film/tissue; film/film; nonwoven/nonwoven; nonwoven/woven; nonwoven/knit and nonwoven/tissue. It is also possible to form multi-layered materials so long as they include a first layer 12 and a second layer 14 as further described below.

The first layer 12 as described herein and depicted in FIG. 1, must be made from a material which is capable of being stretched or extended in at least one direction from a first length L1 to a second length L2 with the second length being greater than the first length. During the stretching or extending process, some materials used for the first layer may permanently deform so that upon relaxation of the stretching forces the first layer does not return to its original length L1 but instead retracts from its second length to a third length L3 which is slightly less than the second length but greater than the first length. Generally this retraction is from about 2 to about 20% of the expanded or second length L2 of the first layer. Materials which permanently deform are useful because the first layer can be greatly thinned thereby reducing the cost of the composite. During the stretching or extension of such materials, the first layer should be capable of being deformed from at least about 5 to as much as 1200% or greater of its original or first length. For example, a piece of material one foot in length which is stretched 1200% would have a stretched length of thirteen feet.

Once the first layer has been bonded to the second layer and the composite has relaxed, the newly formed composite should not be capable of stretching more than 25% of the composite's relaxed length L3 without affecting the lamination or bonding of the first layer 12 to the second layer 14. Consequently, in choosing a material for the first layer 12 from the above noted materials, the material must be chosen such that it is capable of being stretched, optionally deformed, and relaxed according the foregoing parameters. In more refined embodiments of the present invention, the first layer can be distinguished from a traditional "elastic" material which is capable of being stretched from a first length to a second length and then retracting back to a length substantially the same as the first length.

The second layer 14 of the present invention can be selected from any one of the foregoing materials indicated as being suitable for the first layer of the present invention. In addition, the material of the second layer 14, unlike the first layer 12, can be elastic in nature though when attached to the first layer, the second layer 14 should be expanded less than the degree of expansion of the first layer.

The purpose of the second layer 14 is to provide the bulkiness in the overall laminate or composite 10 by puckering or gathering when the first layer 12 is allowed to relax or retract from its second length L2 to its third length L3. It is also important to note that in order to attach the first layer 12 to the second layer 14, the second and first layers must be compatible with one another through the use of adhesives, thermobonding, ultrasonic bonding, stitching or other suitable means of attachment. When using adhesives, the adhesives may be water-based, solvent-based, pressure sensitive or hot-melt adhesives.

As can be seen in the cross-section of FIG. 1, the first layer 12 and the second layer 14 are joined to one another at a plurality of separate and spaced apart locations such that there are a plurality of bonded areas 16 and unbonded areas 18. In fact, depending upon the spacing of the bond points 16, the unbonded areas 18 may actually form unbonded pockets between the first layer 12 and the second layer 14. These pockets optionally may be filled with particulate or fiberous material such as a superabsorbent. Bonding of the first layer 12 to the second layer 14 may be achieved through any number of suitable means including, but not limited to, heat activated and solvent-based adhesives, as well as the actual fusion of the first layer to the second layer through the use of heat and/or pressure as well as through the use of ultrasonic bonding techniques.

Figure 2:
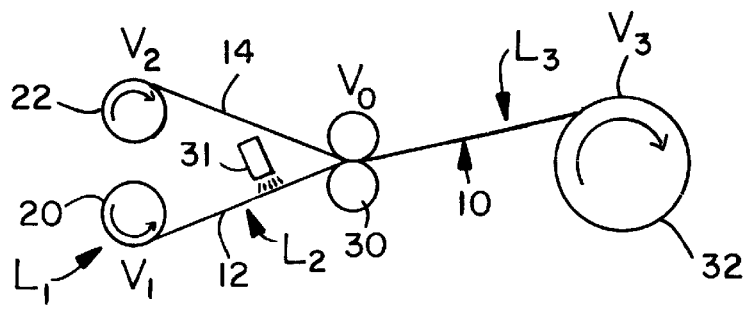
FIG. 2 is a schematic side view of one process for forming a stretch-pillowed laminate according to the present invention.
Figure 3:
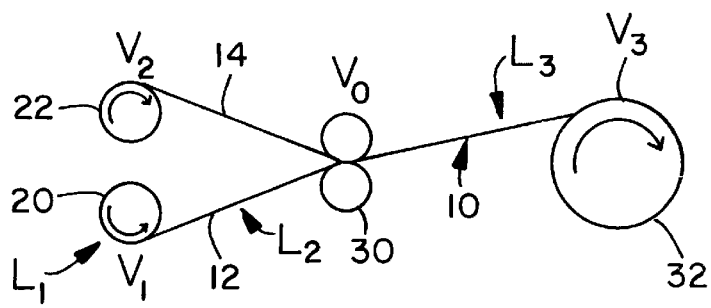
FIG. 3 is a schematic side view of another process for forming a stretch-pillowed laminate according to the present invention.

The process for forming the material 10 of the present invention is shown in schematic form in FIGS. 2 and 3 of the drawings. For purposes of illustration only, the first layer 12 is described as being a thermoplastic film such as polypropylene film and the second layer 14 is a layer of nonwoven spunbonded material made from extruded polypropylene fibers. The material of the first layer 12 is shown as being unwound from a supply roll 20 though it is possible when using films with the present invention to extrude the film in line as part of the process. The second layer 14 as shown in FIGS. 2 and 3 is unwound from a second supply roll 22 and, along with the first layer 12, is sent through a bonder 30. To create stretch in the first layer 12, the first supply roll 20 is driven or retarded at a first speed V1 and the second supply roll 22 is driven at a second speed V2 while the take-up roll 32 is driven or retarded at a third speed V3. At the point of bonding at the bonder 30, the first layer 12 and the second layer 14 have a common speed V0. Prior to the bonder 30 the speed V2 of the second layer 14 can be less than or equal to V0 but in either event V1 is less than V2. By running the first supply roll 20 at a slower rate than second supply roll 22 there is a stretch imparted to the first layer 12 such that the film of first layer 12 is stretched at least 5% beyond its original length. While the first layer 12 is in its stretched state, the second layer 14 is bonded to the first layer 12. In FIG. 2, the first and second layers 12 and 14 are shown being bonded to one another through the use of adhesive and pressure via bonding equipment 30, including an anvil roll and a pattern/smooth roll, and an adhesive sprayer 31, both of which are well known to those of ordinary skill in the art. Alternatively, as shown in FIG. 3, the adhesive sprayer 31 may be deleted in which case it is desirable to apply heat to one or both of the bonding rolls 30. Also, when using only heat and pressure to bond the layers together, it should be remembered that the two layers should be made of materials which are compatible with one another. The bonding equipment 30 serves to bond the two layers to one another across the width of the material in the cross-machine direction. By selecting the bond pattern on the pattern roll, the bond points 16 can be spaced at regular or irregular distances from one another along the material 10 in the machine-direction so that there are a plurality of bonded 16 and unbonded 18 sites along the length of the material as shown in cross-section in FIG. 1. Alternatively, the bond points 16 may be continuous lines of bonding which are parallel or skewed and which can be intersecting or non-intersecting.

Once the first and second layers 12 and 14 have been bonded to one another, the composite 10 is wound around a take-up roll 32 which is traveling at a speed V3 which is less than the speed V2 of second supply roll 22. As a result, the composite material 10 can relax from the stretched state between the supply rolls 20 and 22 and the bonder 30 to a relaxed condition beyond the bonder 30 so that the composite material 10 can be wound on take-up roll 32. As the composite material 10 relaxes between the bonder 30 and the take-up roll 32, the first layer 12 relaxes from between about 2 and about 20% of the expanded length between the first supply roll 20 and the bonder 30 thereby causing the second layer 14 to gather up or pillow as shown in FIG. 1 to create a three-dimensional structure as compared to a simple two-ply laminate. Alternatively, the take-up roll 32 can be driven at the same speed as the bonder 30 in which case the composite material 10 will be wound-up while still in a stretched state. In this case the material 10 will relax slightly while on the roll 32 and the remainder of the relaxation can be achieved as the composite 10 is unwound from the roll 32.

As mentioned previously, when using film as the first layer, the first layer may be stretched to many times its original length, in fact as much as 1200% or more. During such stretching the film will usually permanently deform. An important feature of the present invention is the fact that the first layer 12 can be permanently deformed during the stretching process between first supply roll 20 and the bonder 30. Again referring to FIGS. 2 and 3, while on the supply roll 20, the first layer 12 has a first length L1. Due to the differential speed between the first supply roll 20 and bonder 30, first layer 12 is stretched to a second length L2 with L2 being greater than L1. Depending upon the particular material being used for first layer 12, the degree of stretching necessary to permanently deform first layer 12 may be as little as 5% to as high as 1200% especially when using various plastic films as the first layer 12. In any event, however, it should be remembered that in extending the first layer from L1 to L2 it is sometimes desirable that the material of first layer 12 be permanently deformed so that upon relaxation after the bonder 30, the relaxed length L3 is slightly less than the stretched length L2 but much greater than the original or first length L1 due to the permanent deformation of the material during the stretching process. As a result, the cost of the overall material may be reduced due to the savings in the film layer.

In FIGS. 2 and 3 of the drawings, the material 10 of the present invention is shown as being made into a two ply laminate with stretch and relaxation being imparted in only one direction (the machine direction). With the equipment available today it is also possible to stretch the first layer 12 in more than two directions which may be offset with respect to one another at any desired angle including right angles and angles greater than or less than 90°. Besides stretching the first layer 12, the second layer 14 can also be stretched before the two layers are laminated together. It is desirable, however, that the degree of extension or stretching of the second layer 14 be less than that of the first layer 12. The stretching of the second layer 14 can be substantially parallel to the direction of extension of the first layer 12 or it can be non-parallel or even perpendicular to the direction of extension of the first layer 12.

It is also possible to create materials 10 which are multilayered laminates. As explained earlier, the second layer 14 may itself be made from a laminate of several layers such as a composite of spunbond/meltblown/spunbond materials bonded to one another prior to the composite being bonded to the first layer 12. The same is true with respect to the first layer 12.

Figure 4:
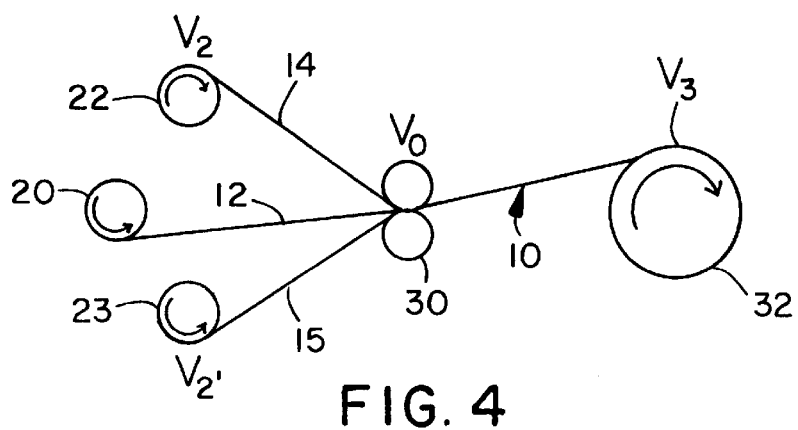
FIG. 4 is a schematic side view of yet another process for forming a stretch-pillowed laminate according to the present invention.
Figure 7:
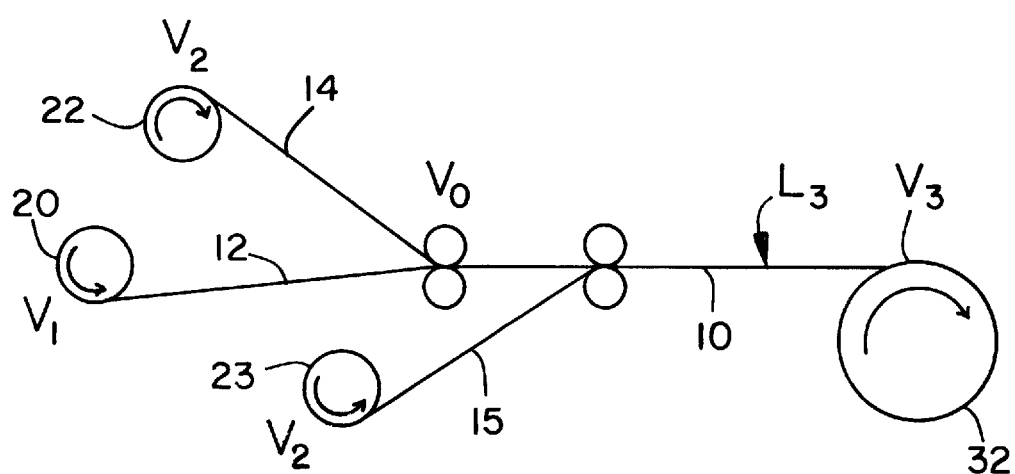
FIG. 7 is a schematic side view of yet another process for forming a stretch-pillowed laminate according to the present invention.

Referring to FIGS. 4 and 7 which are schematics of alternate processes according to the present invention, it also is possible to create a laminate with three or more layers. As shown in FIGS. 4 and 7, the process equipment in operation is identical to that of FIG. 3 except for the addition of a third layer 15 bonded to the side of first layer 12 opposite that of second layer 14. The third layer 15 in its simplest construction can be laminated to the first layer 12 in an unstretched state. Conversely, the third layer 15, as with the second layer 14, may be stretched in a direction either parallel or non-parallel to the direction of stretch of the first and second layers prior to its being bonded to the first layer 12.

As with the process shown in FIG. 3, in the process of FIG. 4, first layer 12 is unwound from supply roll 20, second layer 14 is unwound from supply roll 22 and third layer 15 is unwound from supply roll 23. While first layer 12 is in a stretched and optionally a permanently deformed condition between supply roll 12 and bonder 30, second layer 14 and third layer 15 are bonded at a plurality of separate and spaced apart locations to the opposites sides of first layer 12 via the heated pattern and anvil bond rolls 30. After the three layers have been joined to one another to form the composite 10, the composite 10 is allowed to relax between the bonder 30 and the take-up roll 32 thereby creating a material similar to that shown in cross-section in FIG. 5 of the drawings.

Figure 5:
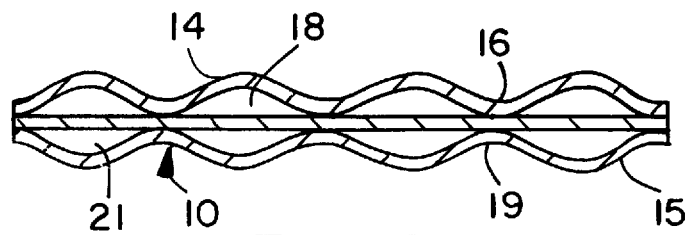
FIG. 5 is a cross-sectional side view of another stretch-pillowed laminate according to the present invention.

In FIG. 5, the third layer 15 is attached to the first layer 12 at a plurality of spaced apart and separate bond sites 19 which are in vertical registry with the bond sites 16 of the second layer 14. As with the unbonded regions 18 between the first layer 12 and the second layer 14, there is also created a plurality of unbonded areas 21 between the third layer 15 and the first layer 12.

Figure 6:
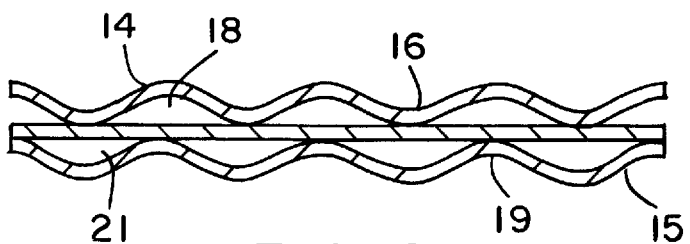
FIG. 6 is a cross-sectional side view of yet another stretch-pillowed laminate according to the present invention.

Referring to FIG. 6, it is also possible to create a material 10 from three layers wherein the bond sites 16 and 19 are not in vertical registry with one another. This is possible by using two separate sets of bonding equipment 30 and 30' as shown in FIG. 7. In FIG. 7 the process is the same as that shown in FIG. 4 except for the use of two pieces of bonding equipment 30 and 30'. The bonding equipment 30 is used to create a first plurality of bond site 16 as shown in FIG. 6 between the first layer 12 and the second layer 14. While the first layer 12 is still in a stretched and deformed condition, a second piece of bonding equipment 30' is used to bond the third layer 15 to the first layer 12 at a second plurality of bond sites 19 (see FIG. 6) which are not in vertical registry with the bond sites 16.

Given the wide number of materials possible with the present invention, a number of example materials were made as described in further detail below.

EXAMPLE 1

The stretch-pillowed laminate material according to the present invention in Example 1 was formed using a 0.65 mil soft polypropylene film layer as the first or extensible layer of the composite. The polypropylene film layer was made from a Himont Catalloy polypropylene resin from Himont U.S.A., Inc. of Wilmington, Del. and had a basis weight of 0.48 ounces per square yard (osy). The second or bulked layer was a polypropylene spunbond nonwoven web made by Kimberly-Clark Corporation of Neenah, Wis. using an Exxon 3445 polypropylene resin from Exxon Chemical Company of Houston, Tex. The spunbond polypropylene nonwoven web utilized 1 to 3 denier fibers, had a basis weight of 0.43 ounces per square yard and was prebonded with an overall bond area of 15%. The film and nonwoven web were subjected to a bonding process similar to that shown in FIG. 2. The film was bonded to the nonwoven layer using a National 34-5541 hot melt adhesive from National Starch and Chemical Company, a subsidiary of Unilever United States, Inc., of New York, N.Y., at an application rate of 0.009 ounces per square yard using a swirl pattern application dye. As shown in Table 1, the extensible polypropylene film layer was driven at a speed V1 of 143 feet per minute, the spunbond web layer was traveling at a speed V2 of 165 feet per minute and at the point of lamination the composite was traveling at a speed V0 of 165 feet per minute. On the winder roll the composite was being taken-up at a speed V3 of 163 feet per minute. In Example 1 the film was stretched 15% beyond its original or first length L1 before the nonwoven web layer was bonded to the film layer. The stretched length corresponded to the second length L2 discussed above. After the bonding process the film/nonwoven web composite was allowed to retract from its second length L2 to a third length L3. As can be seen in Table 1, the bulk $B_2$ of the stretched composite laminate was 0.0275 inches and the basis weight ($BW_2$) was 1.160 ounces per square yard. This in comparison to the bulk ($B_1$) and the basis weight ($BW_1$) of the materials as if they were in a non-stretched state in which case the bulk ($B_1$) would be 0.0108 inches and the basis weight ($BW_1$) would be 0.915 ounces per square yard. To calculate the percent change in both bulk and basis weight between the non-stretched and stretched (bulked) materials the following formulas were used:

$$\% \text{ Bulk Change} = \frac{B_2 - B_1}{B_1} \times 100$$

$$\% \text{ Bulk Weight Change} = \frac{BW_2 - BW_1}{BW_1} \times 100$$

Thus the percent change in bulk was [(0.0275−0.0108)/0.0108]×100 or 154% and the percent change in basis weight was [(1.160−0.915)/0.915]×100 or 26% which represented an increase in both the bulk and basis weight of the bulked and stretched laminate as opposed to a non-bulked and non-stretched material.

The percent stretch and percent recovery for the composite material of Example 1 were calculated using the following equations:

$$\% \text{ Stretch} = \frac{V_0 - V_1}{V_1} \times 100$$

$$\% \text{ Recovery} = \frac{V_0 - V_3}{V_0 - V_1} \times 100$$

Thus the percent stretch for the material of Example 1 was [(165−143)/143]×100 or 15% while the percent recovery was [(165−165)/(165−143)]×100 or 9%. Consequently, the film layer was stretched 15 percent beyond its unstretched length, the nonwoven layer was bonded to it and the composite recovered 9 percent of the 15 percent that the film was stretched thereby causing the bulking of the composite.

Once the composite had been formed, a sample of it was tested to see how much strain the sample could be placed under before it delaminated. As state earlier, the material of the present invention is to be distinguished from composite materials wherein the composite is still elastic once formed. As a result, it is desirable that the material of the present invention once formed not be able to stretch more than 25 percent beyond its relaxed or finished length L3 without adversely affecting the material. To determine this, a simple test was run.

First, a three inch by five inch sample was cut and clamped between the jaws of an Instron tensile machine set with a jaw separation of three inches. It is important to note that the five inch length was parallel to the stretch direction of the first layer of the composite. Next the jaws were expanded at a rate of fifty inches per minute until the gap between the jaws has been expanded from three inches to three and three quarter inches, an expansion of twenty-five percent. Once this gap distance had been achieved, the machine was stopped and the sample was held for one minute before the tension was released and the sample was removed from the jaws. The sample length was then measured and the sample was visually examined for signs of failure, including delamination between the layers and/or a breakdown in structure of the individual layers. A visual examination of the material of Example 1 showed that the material had failed, thus demonstrating that the sample was not elastic.

TABLE 1

| EXAMPLE: ADHESIVE/NONWOVEN/FILM | | |
|---|---|---|
| EXTENSIBLE LAYER: | 0.65 mil softpolypropylene | V1 = 143 |
| BULKED LAYER: | 0.43 oz/yd2 Polypropylene Spunbond | V2 = 165 |
| LAMINATION: | 0.009 oz/yd2 Hot Melt Adhesive | V0 = 165<br>V3 = 163 |
| | Adhesive applied by a swirl pattern die | |
| BULK ENHANCEMENT: | | |
| Nonstretched Laminate | Bulk ($B_1$): 0.0108"<br>Basis Weight ($BW_1$): 0.915 oz/yd2 | |
| Stretched Laminate | Bulk ($B_2$): 0.0275"<br>Basis Weight ($BW_2$): 1.160 oz/yd2 | |
| % Change | Bulk: 154%<br>Basis Weight: 26% | |
| % STRETCH: | $\frac{165-143}{143} * 100 = 15\%$ | |
| % RECOVERY: | $\frac{165-163}{165-143} * 100 = 9\%$ | |

Laminate Testing: Laminate failed at or before 25% elongation.

EXAMPLE 2

In Example 2, the stretch-pillowed laminate material according to the present invention was formed using the same film as described in Example 1. The second or bulked layer was a 0.55 osy thermally bonded carded web which used Scott 6714 2.2 denier polypropylene staple fiber from the Scott Paper Company of Philadelphia, Pa. The film and nonwoven web were subjected to a bonding process similar to that shown in FIG. 3. The calender rolls used to bond the two layers together included a pattern roll heated to a temperature of 245° F. and an anvil roll heated to a temperature of 230° F. with the nip pressure being 20 lbs. per square inch. As shown in Table 2, the extensible polypropylene film layer was driven at a speed V1 of 5 feet per minute, the spunbond web layer was traveling at a speed V2 of 26 feet per minute and at the point of lamination the composite was traveling at a speed V0 of 26 feet per minute. On the winder roll the composite was being taken-up at a speed V3 of 23 feet per minute. In Example 2, the film was stretched 420% beyond its original or first length L1 before the nonwoven web layer was bonded to the film layer. The stretched length corresponded to the second length L2 discussed above. After the bonding process the film/nonwoven web composite was allowed to retract from its second length L2 to a third length L3. As can be seen in Table 2, the bulk ($B_2$) of the stretched composite laminate was 0.018 inches and the basis weight ($BW_2$) was 0.80 ounces per square yard. This is in comparison to the bulk ($B_1$) and basis weight ($BW_1$) of the materials as if they were in a non-stretched state in which case the bulk ($B_1$) would be 0.00455 inches and the basis weight ($BW_1$) would be 0.836 ounces per square yard.

Using the formulas denoted in Example 1, the percent change in bulk was 300% and the percent change in basis weight was 22% which represented an increase in the bulk and a decrease basis weight of the bulked and stretched laminate as opposed to a non-bulked and non-stretched material. The percent stretch for the material of Example 2 was 420% and the percent recovery was 14%. Consequently, the film layer was stretched 420% beyond its unstretched length, the nonwoven layer was bonded to the film and the composite recovered 14% of the 420% that the film was stretched thereby causing the bulking of the composite.

Once the composite had been formed, a sample of it was tested for failure. As with Example 1, the material failed at or before the elongation of 25%.

TABLE 2

EXAMPLE: THERMALLY BONDED NONWOVEN/FILM

| | | |
|---|---|---|
| EXTENSIBLE LAYER: | 0.65 mil soft polypropylene | V1 = 5 |
| BULKED LAYER: | 0.55 oz/yd2 pp Staple/Thermal Bonded Carded Web | V2 = 26 |
| LAMINATION: | Thermal Point Bonded | V0 = 26 |
| | (13% Bond Area) | V3 = 23 |
| Process Conditions: | Pattern Roll Temperature: | 245° F. |
| | Anvil Roll Temperature: | 230° F. |
| | Nip Pressure: | 20 psi |
| BULK ENHANCEMENT: | | |
| Nonstretched Laminate | Bulk ($B_1$): 0.00455" | |
| | Basis Weight ($BW_1$): 1.026 oz/yd2 | |
| Stretched Laminate | Bulk ($B_2$): 0.018" | |
| | Basis Weight ($BW_2$): 0.80 oz/yd2 | |
| % Change | Bulk: 300% | |
| | Basis Weight: 22% | |
| % STRETCH: | $\frac{26-5}{5} * 100 = 420\%$ | |
| % RECOVERY: | $\frac{26-23}{26-5} * 100 = 14\%$ | |

Laminate Testing: Laminate failed at or before 25% elongation.

EXAMPLE 3

In Example 3 a stretch-pillowed laminate material according to the present invention was formed using a 0.65 mil film layer which was the same as that described in Example 1. The second or bulked layer was a polypropylene spunbond nonwoven web made by the Kimberly-Clark Corporation of Neenah, Wis. using an Exxon 3445 polypropylene resin from Exxon Chemical Company of Houston, Tex. The spunbond polypropylene nonwoven web utilized fibers having a denier of approximately 1.3. The web had a basis weight of 0.3 ounces per square yard and the web was prebonded with an overall bond area of 12%. The film and nonwoven web were subjected to a thermal bonding process such as is shown in FIG. 3. Referring to Table 3, the extensible polypropylene film layer was driven at a speed V1 of 2.6 feet per minute, the spunbond web layer was traveling at a speed V2 of 27.6 feet per minute and at the point of lamination the composite was traveling at a speed V0 of 31.2 feet per minute. On the winder roll the composite was being taken-up at a speed V3 of 24.5 feet per minute. In Example 3 the film was stretched 1100% beyond its original or first length L1 before the nonwoven web layer was bonded to the film layer. The stretched length corresponded to the second length L2 discussed above. After the bonding process, the film/nonwoven web composite was allowed to retract from its second length L2 to a third length L3. Referring again to Table 3, the bulk ($B_2$) of the stretched composite laminate was 0.014 inches and the basis weight ($BW_2$) was 0.455 ounces per square yard. This is in comparison to a bulk ($B_1$) of 0.0047 inches and basis weight ($BW_1$) of 0.835 osy for the materials as if they were in a non-stretched state. The percent change in both the bulk and basis weight between the non-stretched and stretched (bulked) materials were calculated as in Example 1. The percent change in bulk was 198% and the percent change in basis weight was −45.5%. This represents a net decrease in the basis weight of the material while still showing an increase in the bulk. This was due to the extreme stretching of the film which caused the reduction of basis weight in the film layer and thus a reduction in the overall basis weight of the composite. However, upon bonding of the two layers to one another, there was still a retraction process which caused the nonwoven layer to pucker and gather thereby explaining the increase in bulk.

The percent stretch for the material in Example 3 was 1100% while the percent recovery was 23.4%. Consequently, the film layer was stretched 1100% beyond its unstretched length, the nonwoven layer was bonded to the stretched film and the composite recovered 23.4% of the 1140% that the film was stretched thereby causing the bulking of the composite.

Once the composite has been formed, a sample was tested and failed before reaching an elongation of 25%.

TABLE 3

EXAMPLE: NONWOVEN/FILM

| | | |
|---|---|---|
| EXTENSIBLE LAYER: | 0.65 mil soft polypropylene film | V1 = 2.6 |
| BULKED LAYER: | 0.3 oz/yd2 PP Spunbond (1.3 dpf) | V2 = 27.6 |
| LAMINATION: | Thermal Point Bonded | V0 = 31.2 |
| | (12% Bond Area) | V3 = 24.5 |
| Process Conditions: | Pattern Roll Temperature: | 235° F. |
| | Anvil Roll Temperature: | 226° F. |
| | Nip Pressure: | 22 psi |
| BULK ENHANCEMENT: | | |
| Nonstretched Laminate | Bulk ($B_1$): .0047" | |
| | Basis Weight ($BW_1$): 0.835 oz/yd2 | |
| Stretched Laminate | Bulk ($B_2$): 0.014" | |
| | Basis Weight ($BW_2$): 0.455 oz/yd2 | |
| % Change | Bulk: 198% | |
| | Basis Weight: −45.5% | |
| % STRETCH: | $\frac{31.2-2.6}{2.6} * 100 = 1100\%$ | |
| % RECOVERY: | $\frac{31.2-24.5}{31-2.6} * 100 = 23.4\%$ | |

Laminate Testing: Laminate failed at or before 25% elongation.

EXAMPLE 4

In Example 4, the stretch-pillowed laminate material according to the present invention was formed using two polypropylene spunbond webs. Both webs were made by the Kimberly-Clark Corporation of Neenah, Wis. They each had a basis weight of 0.8 osy and used 3 denier fibers extruded from Exxon polypropylene resin. Each of the webs were individually prebonded with an overall bond area of 15%. The two nonwoven webs were subjected to a bonding process similar to that shown in FIG. 3. The calender rolls used to bond the two layers together included a pattern roll heated to a temperature of 275° F. and an anvil roll heated to a temperature of 275° F. with the nip pressure being 20 lbs. per square inch. As shown in Table 4, one of the polypropylene spunbond nonwoven webs was driven at a speed V1 of 21 feet per minute and the second spunbond web was traveling at a speed V2 of 28 feet per minute. At the point of lamination the composite was traveling at a speed V0 of 28 feet per minute and on the winder roll the composite was being taken-up at a speed V3 of 21 feet per minute. In Example 4, the web traveling at speed V1 (21 ft/min) was stretched 33% beyond its original or first length L1 before the second nonwoven web was bonded to the first web. The stretched length corresponded to the second length L2 discussed above. The two webs were bonded together using thermal point bonding with a 15% total bond area. After the bonding process the nonwoven/nonwoven web composite was allowed to retract from its second length L2 to a third length L3. As can be seen in Table 4, the bulk ($B_2$) of the stretched composite laminate was 0.0465 inches and the basis weight ($BW_2$) was 1.77 ounces per square yard. This is in comparison to a bulk ($B_1$) of 0.0162 inches and basis weight ($BW_1$) of 1.6 osy if the materials were in a non-stretched state.

Using the formulas denoted in Example 1, the percent change in bulk was 187% and the percent change in basis weight was 10% which represented an increase in both the bulk and basis weight of the bulked and stretched laminate as opposed to a non-bulked and non-stretched material. The percent stretch for the material of Example 4 was 33% and the percent recovery was 100%. Consequently, the first nonwoven web was stretched 33% beyond its unstretched length, the second nonwoven web was bonded to the first and the composite recovered 100% of the 33% that the first nonwoven web layer was stretched thereby causing the bulking of the composite.

Once the composite had been formed, a sample was tested for delamination. This sample also delaminated at or before being elongated 25%.

TABLE 4

EXAMPLE: NONWOVEN/NONWOVEN

| | | |
|---|---|---|
| EXTENSIBLE LAYER: | 0.8 yd2 PP Spunbond (3 dpf) | V1 = 21 |
| BULKED LAYER: | 0.8 oz/yd2 Polypropylene Spunbond | V2 = 28 |
| LAMINATION: | Thermal Point Bonded | V0 = 28 |
| | (15% Bond Area) | V3 = 21 |
| Process Conditions: | Pattern Roll Temperature: | 275° F. |
| | Anvil Roll Temperature: | 275° F. |
| | Nip Pressure: | 20 psi |
| BULK ENHANCEMENT: | | |
| Nonstretched Laminate | Bulk ($B_1$): 0.0162" | |
| | Basis Weight ($BW_1$): 1.6 oz/yd2 | |
| Stretched Laminate | Bulk ($B_2$): 0.0465" | |
| | Basis Weight ($BW_2$): 1.77 oz/yd2 | |
| % Change | Bulk: 187% | |
| | Basis Weight: 10% | |
| % STRETCH: | $\frac{28-21}{21} * 100 = 33\%$ | |
| % RECOVERY: | $\frac{28-21}{28-21} * 100 = 100\%$ | |

Laminate Testing: Laminate failed at or before 25% elongation.

EXAMPLE 5

In Example 5, the stretch-pillowed laminate material according to the present invention was formed using the same film as described in Example 1. Unlike the other examples, however, in this example a bulked nonwoven layer was attached to either side of the film layer as shown in FIG. 5 thereby forming a three layer structure. Both of the spunbond nonwoven webs were made by the Kimberly-Clark Corporation of Neenah, Wis. using Exxon polypropylene. The bottom spunbond polypropylene nonwoven web utilized 2.2 denier fibers, had a basis weight of 0.4 osy and was thermally prebonded with an overall bond area of 15%. The top spunbond polypropylene nonwoven web utilized 1.8 denier fibers, had a basis weight of 0.35 osy and was thermally prebonded with an overall bond area of 15%. The film and nonwoven webs were subjected to a bonding process similar to that shown in FIG. 4. The calender rolls used to bond the three layers included a pattern roll heated to a temperature of 275° F. and an anvil roll heated to a temperature of 275° F. with the nip pressure being 25 lbs. per square inch. The total thermal point bond area of the overall structure was 15%. As shown in Table 5, the extensible polypropylene film layer was driven at a speed V1 of 3.5 feet per minute, the spunbond web layers were each traveling at speeds V2 and V2' respectively of 37 feet per minute and at the point of lamination the composite was traveling at a speed V0 of 37 feet per minute. On the winder roll the composite was taken-up at a speed V3 of 35 feet per minute. In Example 5, the film was stretched 960% beyond its original or first length L1 before the nonwoven web layers were bonded to either side of the film layer. The stretched length corresponded to the second length L2 discussed above. After the bonding process the nonwoven/film/nonwoven web composite was allowed to retract from its second length L2 to a third length L3. As can be seen in Table 5, the bulk ($B_2$) of the stretched composite laminate was 0.019 inches and the basis weight ($BW_2$) was 1.02 ounces per square yard. This is in comparison to the bulk ($B_1$) and basis weight ($BW_1$) of the materials as if they were in a non-stretched state in which case the bulk ($B_1$) would be 0.0117 inches and the basis weight ($BW_1$) would be 1.226 ounces per square yard.

Using the formulas denoted in Example 1, The percent stretch for the material of Example 5 was 960% and the percent recovery was 6%. The percent change in bulk was 63% and the percent change in basis weight was −17%. This represents a net decrease in the basis weight of the composite material while still showing an increase in bulk. This was due to the extreme stretching of the film which caused the reduction in basis weight. However, upon the bonding together of the three layers, there was still a retraction of 6% which caused the nonwoven layers to gather up thereby increasing the bulk.

Once the composite had been formed, a sample was tested for delamination and failed at or before it reached an elongation of 25%.

TABLE 5

EXAMPLE: NONWOVEN/FILM/NONWOVEN

| | | |
|---|---|---|
| EXTENSIBLE LAYER: | 0.65 mil soft polypropylene | V1 = 3.5 |
| TOP BULKED LAYER: | 0.35 oz/yd2 PP Spunbond (1.8 dpf) | V2 = 37 |
| BOTTOM BULKED LYR: | 0.4 oz/yd2 PP Spunbond (2.2 dpf) | V2 = 37 |
| LAMINATION: | Thermal Point Bonded | V0 = 37 |
| | (15% Bond Area) | V3 = 35 |
| Process Conditions: | Pattern Roll Temperature: | 275° F. |
| | Anvil Roll Temperature: | 275° F. |
| | Nip Pressure: | 25 psi |

TABLE 5-continued

EXAMPLE: NONWOVEN/FILM/NONWOVEN

BULK ENHANCEMENT:

| | |
|---|---|
| Nonstretched Laminate | Bulk ($B_1$): 0.0117" |
| | Basis Weight ($BW_1$): 1.226 oz/yd2 |
| Stretched Laminate | Bulk ($B_2$): 0.019" |
| | Basis Weight ($BW_2$): 1.02 oz/yd2 |
| % Change | Bulk: 63% |
| | Basis Weight: −17% |
| % STRETCH: | $\frac{37-3.5}{3.5} * 100 = 960\%$ |
| % RECOVERY: | $\frac{37-35}{37-3.5} * 100 = 6\%$ |

Laminate Testing: Laminate failed at or before 25% elongation.

EXAMPLE 6

In Example 6, the stretch-pillowed laminate material according to the present invention included a 0.6 mil ethylene-maleic anhydride (EMA) cast film using Chevron 2207 EMA polymer from the Chevron Corporation of San Francisco, Calif. The second or bulked layer was a 0.36 osy thermally bonded carded web made by Streans Canada, Inc., of Mississauga, Ontario, Canada, using T176 polypropylene fibers (2.2 denier) from Hercules Canada, Iberville, Quebec, Canada. The film and bonded carded web were subjected to a bonding process similar to that shown in FIG. 3. The calender rolls used to bond the two layers together included a pattern roll heated to a temperature of 200° F. and an anvil roll heated to a temperature of 150° F. with the nip pressure being 25 lbs. per square inch. As shown in Table 6, the extensible EMA film layer was driven at a speed V1 of 12 feet per minute, the bonded carded web layer was traveling at a speed V2 of 23 feet per minute and at the point of lamination the composite was traveling at a speed V0 of 23 feet per minute. On the winder roll the composite was taken-up at a speed V3 of 21 feet per minute. In Example 6, the film was stretched 92% beyond its original or first length L1 before the bonded carded web layer was bonded to the film layer. The stretched length corresponded to the second length L2 discussed above. After the bonding process the film/nonwoven web composite was allowed to retract from its second length L2 to a third length L3. As can be seen in Table 6, the bulk ($B_2$) of the stretched composite laminate was 0.015 inches and the basis weight ($BW_2$) was 0.95 ounces per square yard. This is in comparison to a bulk ($B_1$) of 0.005 inches and basis weight ($BW_1$) of 0.82 osy if the materials were in a non-stretched state.

Using the formulas denoted in Example 1, the percent change in bulk was 200% and the percent change in basis weight was 15.8% which represented an increase in both the bulk and basis weight of the bulked and stretched laminate as opposed to a non-bulked and non-stretched material. The percent stretch for the material was 92% and the percent recovery was 18%. Consequently, the film layer was stretched 92% beyond its unstretched length, the nonwoven layer was bonded to the film layer and the composite recovered 18% of the 92% that the film was stretched thereby causing the bulking of the composite.

Once the composite had been formed, a sample was tested for delamination and once again the sample failed thereby demonstrating that the composite was not elastic.

TABLE 6

EXAMPLE: NONWOVEN/FILM

| EXTENSIBLE LAYER: | 0.6 mil EMA Cast Film | V1 = 12 |
|---|---|---|
| BULKED LAYER: | 0.36 oz/yd2 PP Staple TBCW | V2 = 23 |
| LAMINATION: | Thermal Point Bonded | V0 = 23 |
| | (15% Bond Area) | V3 = 21 |
| Process Conditions: | Pattern Roll Temperature: | 200° F. |
| | Anvil Roll Temperature: | 150° F. |
| | Nip Pressure: | 25 psi |

BULK ENHANCEMENT:

| | |
|---|---|
| Nonstretched Laminate | Bulk ($B_1$): 0.005" |
| | Basis Weight ($BW_1$): 0.82 oz/yd2 |
| Stretched Laminate | Bulk ($B_2$): 0.015" |
| | Basis Weight ($BW_2$): 0.95 oz/yd2 |
| % Change | Bulk: 200% |
| | Basis Weight: 15.8% |
| % STRETCH: | $\frac{23-12}{12} * 100 = 92\%$ |
| % RECOVERY: | $\frac{23-21}{23-12} * 100 = 18\%$ |

Laminate Testing: Laminate failed at or before 25% elongation.

EXAMPLE 7

In Example 7, the stretch-pillowed laminate material according to the present invention was formed using a 0.6 mil soft polypropylene blown film made from Exxtral Reactor TPO polymer from Exxon Chemical Company of Houston, Tex. The second or bulked layer was a 0.36 ounce per square yard polypropylene staple fiber thermally bonded carded web used in Example 6. The film and bonded carded web were subjected to a bonding process similar to that shown in FIG. 3. The calendar rolls used to bond the two layers together included a pattern roll heated to a temperature of 250° F. and an anvil roll heated to a temperature of 210° F. with the nip pressure being 25 pounds per square inch. As shown in Table 7, the extensible polypropylene film layer was driven at a speed V1 of 3 feet per minute, the bonded carded web was traveling at a speed V2 of 10 feet per minute and at the point lamination the composite was traveling at a speed V0 of 10 feet per minute. On the winder roll the composite was taken-up at a speed V3 of 9 feet per minute. In Example 7, the film was stretched 233% beyond its original or first length L1 before the nonwoven layer was bonded to the film layer. The stretched length corresponded to the second length L2 discussed above. After the bonding process the film/nonwoven web composite was allowed to retract from its second length L2 to a third length L3. Referring to Table 7, the bulk ($B_2$) of the stretched composite was 0.041 inches and the basis weight ($BW_2$) was 0.82 ounces per square yard. This is in comparison to a bulk ($B_1$) of 0.005 inches and a basis weight of ($BW_1$) of 0.69 ounces per square yard if the materials were in a non-stretched state.

Again using the formulas noted in Example 1, the percent change in bulk was 720% and the percent change in basis weight was 18.8%. This represented an increase in both the bulk and basis weight of the bulked and stretched laminate as opposed to a non-bulked and non-stretched material. The percent stretch for the material of Example 7 was 233% and the percent recovery was 14%. Consequently, the film layer was stretched 233% beyond its unstretched length, the nonwoven layer was bonded to the film and the composite recovered 14% of the 233% that the film was stretched thereby causing the bulking of the composite.

Once the composite had been formed, a sample was tested to see how much strength the sample could be placed under before delamination. Again the sample delaminated when stretched 25%.

TABLE 7

EXAMPLE: NONWOVEN/FILM

| EXTENSIBLE LAYER: | 0.6 mil Soft PP Blown Film | V1 = 3 |
|---|---|---|
| BULKED LAYER: | 0.36 oz/yd2 PP Staple TBCW | V2 = 10 |
| LAMINATION: | Thermal Point Bonded | V0 = 10 |
| | (15% Bond Area) | V3 = 9 |
| Process Conditions: | Pattern Roll Temperature: | 250° F. |
| | Anvil Roll Temperature: | 210° F. |
| | Nip Pressure: | 25 psi |
| BULK ENHANCEMENT: | | |
| Nonstretched Laminate | Bulk ($B_1$): 0.005" | |
| | Basis Weight ($BW_1$): 0.69 oz/yd2 | |
| Stretched Laminate | Bulk ($B_2$): 0.041" | |
| | Basis Weight ($BW_2$): 0.82 oz/yd2 | |
| % Change | Bulk: 720% | |
| | Basis Weight: 18.8% | |
| % STRETCH: | $\frac{10-3}{3} * 100 = 233\%$ | |
| % RECOVERY: | $\frac{10-9}{10-3} * 100 = 14\%$ | |

Laminate Testing: Laminate failed at or before 25% elongation.

EXAMPLE 8

In Example 8 the first or extensible layer was formed from a 0.6 mil soft polypropylene blown film made from Eastman Reactor TPO P6-005 polymer from Eastman Chemicals Division of Eastman Kodak Company of Rochester, N.Y. The second or bulked layer was the same material as used in Example 7. The film and bonded carded web were subjected to a bonding process similar to that shown in FIG. 3. The temperature of the pattern and anvil rolls as well as the nip pressure were the same as those in Example 7. Referring to Table 8, the extensible polypropylene film layer was driven at a speed V1 of 12 feet per minute, the bonded carded web layer was traveling at a speed V2 of 41 feet per minute and at the point of lamination the composite was traveling at a speed V0 of 41 feet per minute. The laminate taken-up on the winder roll had a percent bond area of 15% and was taken-up at a speed V3 of 36 feet per minute. The film layer was stretched 242% beyond its original or first length L1 before the bonded carded web was bonded to the film layer. The stretched length corresponded to the second length L2 discussed above. After the bonding process the film/nonwoven web composite was allowed to retract from its second length L2 to a third length L3. As can bee seen in Table 8, the bulk ($B_2$) of the stretched composite laminate was 0.018 inches and the basis weight ($BW_2$) was 0.71 ounces per square yard. This is in comparison to a bulk ($B_1$) of 0.005 inches and a basis weight ($BW_1$) of 0.75 ounces per square yard for the materials as if they were in a non-stretched state.

Using the formulas from Example 1, the percent change in bulk was 260% and the percent change in basis weight was a −5%. This represented a net decrease in the basis weight of the material while still showing an increase in bulk. As with Example 3, the negative basis weight of the composite was due to the extreme stretching of the film layer. The percent stretch for the material in Example 8 was 242% and the percent recovery was 17%. Consequently, the film layer was stretched 242% beyond its unstretched length, the nonwoven layer was bonded to the film and the composite recovered 17% of the 242% that the film was stretched thereby causing the bulking of the composite.

TABLE 8

EXAMPLE: NONWOVEN/FILM

| EXTENSIBLE LAYER: | 0.65 mil soft PP blown film | V1 = 12 |
|---|---|---|
| BULKED LAYER: | 0.36 oz/yd2 PP Staple TBCW | V2 = 41 |
| LAMINATION: | Thermal Point Bonded | V0 = 41 |
| | (15% Bond Area) | V3 = 36 |
| Process Conditions: | Pattern Roll Temperature: | 250° F. |
| | Anvil Roll Temperature: | 210° F. |
| | Nip Pressure: | 25 psi |
| BULK ENHANCEMENT: | | |
| Nonstretched Laminate | Bulk ($B_1$): 0.005" | |
| | Basis Weight ($BW_1$): 0.75 oz/yd2 | |
| Stretched Laminate | Bulk ($B_2$): 0.018" | |
| | Basis Weight ($BW_2$): 0.71 oz/yd2 | |
| % Change | Bulk: 260% | |
| | Basis Weight: −5% | |
| % STRETCH: | $\frac{41-12}{12} * 100 = 242\%$ | |
| % RECOVERY: | $\frac{41-36}{41-12} * 100 = 17\%$ | |

Samples of materials similar to the foregoing examples were converted into a prototype diaper construction with the material of the present invention being utilized as the outercover of the diaper. Typical diaper constructions include a liquid pervious top sheet and a substantially liquid impervious backing sheet or outercover. Disposed between the top sheet and the backing sheet is an absorbent core. The soft nonwoven layer of the film/nonwoven laminate was placed on the exterior of the diaper so as to provide a cloth-like outercover. The same film and nonwoven layers were also manufactured into a standard two-ply bonded laminate with no pillowing. This material was also made into diaper outercover. When both the pillowed and non-pillowed diapers were subjected to site and handling panels the stretch-pillowed material of the present invention was found to be more preferred than the simple two-dimensional outercover material. The diaper with the stretch-pillowed material of the present invention was perceived as having more definition, durability and quality. As a result, the material of the present invention when used in conjunction with a diaper yielded a product with a higher acceptance rate than two-dimensional materials. A particularly favorable material according to the present invention included a first layer of 0.5 mil polyethylene film with a 0.7 ounce per square yard spunlace material available from E. I. DuPont de Nemours and Company of Wilmington, Del. and sold under the trademark SONTARA. These two layers were laminated together at a plurality of discrete bond points using 0.3 grams per square yard of a hot melt adhesive identified as H-2096 from Findley Adhesives, Inc. of Wauwatosa, Wis.

The material described in the preceding examples is particularly useful as an outercover material for personal care products, however, it has other applications as outlined previously. In addition, it should be noted that this laminate as well as other laminate combinations may be subjected to additional processing to enhance the overall attributes of the particular composite material. For example, either one or both of the layers in a two layer structure or one or all three of the layers in a three or multi-layer structure may be embossed either before or after laminating/bonding the layers together. In addition, aperturing is also possible. Furthermore, it is possible to interject specific materials between the first and second layers just prior to the bonding process as, for example, fluid handling materials such as superabsorbents to further enhance the overall properties of the present invention.

Having thus described the invention in detail, it should be apparent that various other modifications and changes can be made in the present invention without departing from the spirit and scope of the following appended claims.

We claim:

1. A process for forming a bulked stretch-pillowed laminate comprising:
   a) extending a first extensible layer from an original length to an expanded length, said expanded length being at least 5 percent greater than said original length and said first extensible layer being permanently deformed as a result of said extension;
   b) placing a second layer in juxtaposition with said first layer while said first layer is in said expanded length;
   c) attaching said first and second layers to one another at a plurality of spaced-apart bond sites to form said laminate such that there are a plurality of bonded and unbonded areas; and
   d) allowing said first layer of said laminate to relax to a permanently deformed length which is still longer than said original length but less than said expanded length, said laminate having a plurality of bulked areas in the locations where said first and second layers are unbonded.

2. The process of claim 1 wherein a third layer is attached to said first layer while said first layer is in an expanded state.

3. The process of claim 2 wherein said third layer is attached to said first layer at a plurality of spaced-apart bond sites which are in vertical registry with the bond sites of said first and second layers.

4. The process of claim 2 wherein said third layer is attached to said first layer at a plurality of spaced-apart bond sites which are not in vertical registry with the bond sites of said first and second layers.

5. The process of claim 2 wherein said third layer is extended prior to said first and third layers being attached to one another.

6. The process of claim 1 wherein said deformed length of said first layer is caused by the relaxation of said first layer from said expanded length to a retracted length, with said retracted length being between about 80 and 98% of said expanded length.

7. The process of claim 1 wherein said extension of said first layer is in more than one direction.

8. The process of claim 1 wherein said extension of said first layer takes place in at least two directions which are at substantially right angles to one another.

9. The process of claim 1 wherein said second layer is extended prior to said first and second layers being attached to one another.

10. The process of claim 9 wherein the direction of said extension of said second layer is substantially parallel to the direction of extension of said first layer.

11. The process of claim 9 wherein the direction of said extension of said second layer is substantially non-parallel to the direction of extension of said first layer.

12. The process of claim 1 wherein said first and second layers are attached to one another through the use of heat and pressure.

13. The process of claim 1 wherein said first and second layers are attached to one another through the use of ultrasonic bonding.

14. The process of claim 1 wherein said first and second layers are attached to one another through the use of adhesives, said adhesives being selected from the group consisting of water-based, solvent-based, pressure sensitive and hot-melt adhesives.

15. A bulked, stretch-pillowed laminate comprising:
   a first extensible layer and a second layer, said second layer being attached to said first extensible layer at a plurality of spaced-apart bond sites to form a bulked laminate with a plurality of bonded and unbonded areas, said bulked laminate being bulked due to said second layer having more surface area than said first extensible layer per the same unit area of said laminate, said bulked laminate being capable of stretching no more than twenty-five percent without delamination.

16. The bulked, stretch-pillowed laminate of claim 15 wherein a third layer is attached to said first extensible layer on a side of said first extensible layer opposite said second layer, said third layer being attached to said first extensible layer at a plurality of spaced-apart bond sites to form a plurality of bonded and unbonded areas between said first extensible layer and said third layer, said third layer having more surface area than said first extensible layer per the same unit area of said bulked laminate.

17. The bulked, stretch-pillowed laminate of claim 16 wherein said spaced-apart bond sites of attachment of said second and third layers to said first extensible layer are in vertical registry with one another.

18. The bulked, stretch-pillowed laminate of claim 16 wherein said spaced-apart bond sites of attachment of said second and third layers to said first extensible layer are in non-vertical registry with one another.

19. A personal care absorbent article comprising:
   a liquid pervious top sheet and a backing sheet with an absorbent core disposed between said liquid-pervious top sheet and said backing sheet, said backing sheet being made from a bulked, stretch-pillowed laminate according to claim 15.

20. A personal care absorbent article comprising:
   a liquid-pervious top sheet and a backing sheet with an absorbent core disposed between said liquid-pervious top sheet and said backing sheet, said liquid-pervious top sheet being made from a bulked, stretch-pillowed laminate according to claim 15.

21. The bulked, stretch-pillowed laminate of claim 15 wherein said first extensible layer is a film and said second layer is a fibrous nonwoven web.

22. The bulked, stretch-pillowed laminate of claim 15 wherein said first extensible layer is a film and said second layer is a fibrous nonwoven web, said film defining a plurality of apertures therein.

23. A personal care absorbent article comprising:
   a liquid-pervious top sheet and a backing sheet with an absorbent core disposed between said liquid-pervious top sheet and said backing sheet wherein said liquid-pervious top sheet is made from a bulked, stretch-pillowed laminate according to claim 22.

24. The personal care absorbent article of claim 23 wherein said article is a diaper.

25. The personal care absorbent article of claim 23 wherein said article is a sanitary napkin.

26. The personal care absorbent article of claim 23 wherein said article is a training pant.

27. The personal care absorbent article of claim 23 wherein said article is an incontinence product.

28. A bulked, stretch-pillowed laminate comprising:
   a first extensible layer and a second layer, said second layer being attached said first extensible layer at a plurality of spaced-apart bond sites to form a bulked laminate with a plurality of bonded and unbonded areas, said bulked laminate being bulked due to said second layer having more surface area than said first extensible layer per the same unit area of said bulked laminate, said bulked laminate being capable of stretching not more than 25 percent without affecting the lamination of said first extensible layer to said second layer.

29. The bulked, stretch-pillowed laminate of claim 28 wherein a third layer is attached to said first extensible layer on a side of said first extensible layer opposite said second layer, said third layer being attached to said first extensible layer at a plurality of spaced-apart bond sites to form a plurality of bonded and unbonded areas between said first extensible layer and said third layer, said third layer having more surface area than said first extensible layer per the same unit area of said bulked laminate.

30. The bulked, stretch-pillowed laminate of claim 29 wherein said spaced-apart bond sites of attachment of said second and third layers to said first extensible layer are in vertical registry with one another.

31. The bulked, stretch-pillowed laminate of claim 29 wherein said spaced-apart bond sites of attachment of said second and third layers to said first extensible layer are in non-vertical registry with one another.

32. The bulked, stretch-pillowed laminate of claim 28 wherein said first extensible layer is a film and said second layer is a fibrous nonwoven web.

33. The bulked, stretch-pillowed laminate of claim 28 wherein said first extensible layer is a film and said second layer is a fibrous nonwoven web, said film defining a plurality of apertures therein.

34. A personal care absorbent article comprising:

a liquid-pervious top sheet and a backing sheet with an absorbent core disposed between said liquid-pervious top sheet and said backing sheet wherein said liquid-pervious top sheet is made from a bulked, stretch-pillowed laminate according to claim 28.

35. A personal care absorbent article comprising:

a liquid-pervious top sheet and a backing sheet with an absorbent core disposed between said liquid-pervious top sheet and said backing sheet wherein said liquid-pervious top sheet is made from a bulked, stretch-pillowed laminate according to claim 33.

36. A personal care absorbent article comprising:

a liquid-pervious top sheet and a backing sheet with an absorbent core disposed between said liquid-pervious top sheet and said backing sheet, said backing sheet being made from a bulked, stretch-pillowed laminate according to claim 28.

* * * * *